United States Patent [19]

Murray et al.

[11] 4,224,696
[45] Sep. 30, 1980

[54] PROSTHETIC KNEE

[75] Inventors: Ian Murray, Bellevue, Wash.; Stanley Kampner, San Francisco, Calif.

[73] Assignee: Hexcel Corporation, San Francisco, Calif.

[21] Appl. No.: 940,525

[22] Filed: Sep. 8, 1978

[51] Int. Cl.³ ............................................. A61F 1/03
[52] U.S. Cl. ................................... 3/1.911; 128/92 C
[58] Field of Search ................... 3/1.9, 1.91, 1.911; 128/92 C

[56]  References Cited
U.S. PATENT DOCUMENTS

| | | | |
|---|---|---|---|
| 3,748,662 | 7/1973 | Helfet | 3/1.911 |
| 3,840,905 | 10/1974 | Deane | 3/1.911 |
| 3,869,729 | 3/1975 | Attenborough | 3/1.91 |
| 4,016,606 | 4/1977 | Murray et al. | 3/1.911 |
| 4,064,568 | 12/1977 | Grundei et al. | 3/1.911 |
| 4,081,866 | 4/1978 | Upshaw et al. | 3/1.911 |
| 4,085,466 | 4/1978 | Goodfellow et al. | 3/1.911 X |

Primary Examiner—Clifford D. Crowder
Attorney, Agent, or Firm—Townsend and Townsend

[57]  ABSTRACT

A prosthetic knee having as its component parts a femoral implant, a tibial implant, and a meniscal plate disposed between the implants. Knee flexion and extension is permitted by compoundly curved condyle surfaces of the femoral implant, which resemble corresponding surfaces of a natural knee, and correspondingly shaped convex bearing surfaces in the meniscal plate. All other motions of the prosthetic knee take place at the interface between the meniscal plate and tibial implant. This interface is defined by a continuous, concave, spherically shaped surface in the upwardly facing plateau of the tibial implant and a corresponding, continuous, convex spherical surface of the meniscal plate. The components are biased into mutual engagement along the cooperating concave and convex surfaces by the natural ligaments which surround the prosthetic knee. The continuous biased engagement of the cooperating convex and concave surfaces of the prosthetic knee assure its stability.

20 Claims, 9 Drawing Figures

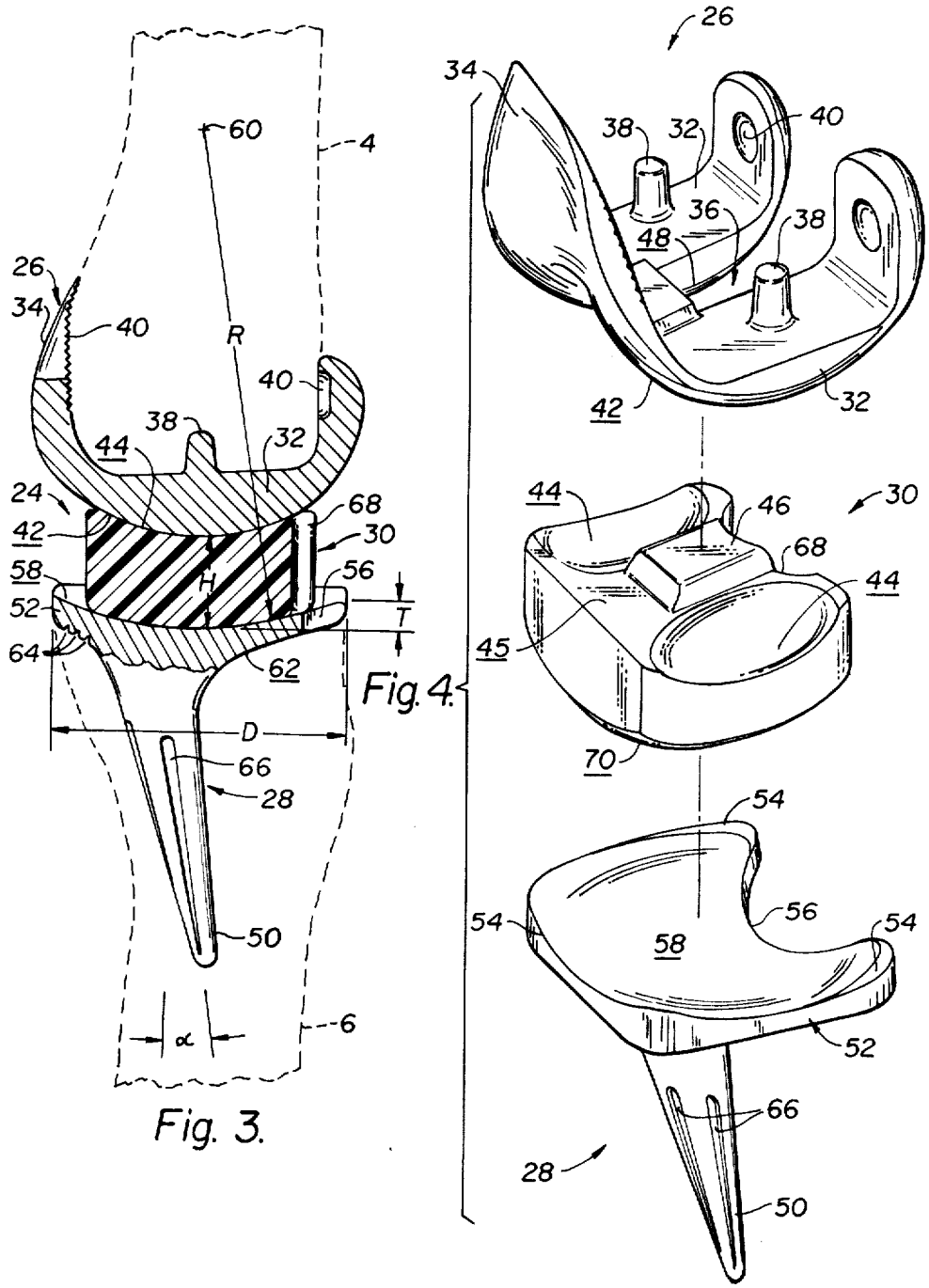

PROSTHETIC KNEE

BACKGROUND OF THE INVENTION

This invention relates to an artificial knee prosthesis, or a prosthetic knee, for the replacement of a natural knee through surgical implantation.

In general, a natural knee is formed by the two condyles of the bottom part of the femur, the lower surfaces of which bear upon the complementarily shaped upper surface plateaus of the tibia through the intermediary of meniscii, a fibro-cartilage. Connection through the knee is provided by means of ligaments which also provide joint stability and help to absorb stresses applied to the knee. The femur, meniscii and tibia are normally subjected to relatively large forces in the course of supporting the major portion of a person's body weight.

Movement of the normal knee is complex, that is it is not simply a pivotal or rotational movement. Rather, a healthy, natural knee has the ability to move in four distinct manners. First, the natural knee joint permits flexion and extension between the femur and the tibia through an arc of about 135°. This motion is a combined rotational, rocking and gliding movement of successive points of the femoral condyles and the tibial plateaus. Secondly, the healthy, natural knee permits a relative rotational movement between the condyles and the tibial plateaus. Thirdly, the knee permits some limited relatively sliding motion which might be described as taking place in a generally horizontal plane between the condyles and the plateau; and fourthly the knee permits a rolling-type motion, frequently referred to as abduction and adduction, between the condyles and the plateaus which might best be described as a limited rocking-type motion in a lateral direction, that is generally perpendicular to the plane in which the knee most commonly articulates (flexion and extension).

Aside from the proper geometric configuration of the condyles and the tibial plateaus, an effective, free movement of a natural knee in these four directions requires the presence of a fibro-cartilage, commonly referred to as meniscus, between the condyles and the plateaus. When the meniscii become damaged, deceased or inflammed, they cease to function properly, the mobility of the knee joint becomes increasingly impaired and movements are accompanied by increasingly severe pains.

To alleviate this condition, it is sometimes necessary to replace the natural knee by surgically implanting a prosthetic knee.

REVIEW OF THE PRIOR ART

The prior art is replete with a great variety of prosthetic knees. In all instances, the prior art seeks to approximate the mobility of a natural knee to a greater or lesser extent by providing artificial substitutes of the condyle surfaces, the condyles as a whole, the entire lower portion of the femur, the tibial plateau or the entire upper portion of the tibia, including the plateau. The following U.S. patents disclose a variety of differently constructed and operating prosthetic knees: U.S. Pat. Nos. 3,715,763; 3,774,244; 3,813,700; 3,824,630; 3,852,830; 3,924,277; 3,964,106; 4,000,525; 4,034,418.

Further, the article "The Surgical Replacement of the Human Knee Joint" by D. A. Sonstegard, L. S. Matthews and H. Kaufer, published in the January 1978 issue (Vol. 238, No. 1) of Scientific American on pages 44–51, gives a good summary of the problems encountered with prosthetic knees and discusses the current state of the art in general terms.

There are two main types of prosthetic knees. The first type is an articulated device which provides a constraining mechanical linkage between the femoral and tibial implants; that is one in which the two implants are mechanically constrained to each other by means of a hinge, a ball and socket type joint, etc.

The second type of prosthetic knee is a non-constrained or unlinked device. In these devices, the emphasis is an replacing some or all of worn and/or deceased load bearing surfaces of the knee. They do not include a mechanical link, hinge, or similar constraint between the femoral and tibial implants. Instead, the stability of the prosthetic knee is primarily provided by the patient's ligaments and muscles. The present invention is of the latter type, that is it may be classified as a non-constrained prosthetic knee.

Generally speaking, the replacement of an entire natural knee requires the surgical implantation of the prosthetic knee by removing at least portions of the femoral condyles and the tibial plateaus and implanting therein normally metallic substitutes referred herein as "femoral implants" and "tibial implants".

Although the exact construction of the femoral and tibial implants of such prostehtic knees and the exact manner in which they are connected to the femur and the tibia, respectively varies, they all have the common characteristic that the implants are placed against the femur and the tibia and secured thereto with a bonding agent or cement. After the implants are in place and cemented to the respective bone structures, ligaments and muscles cooperate with the prosthetic knee and keep the opposing surfaces of the implant in contact. The contraction of appropriate muscles then induces the relative movements between the implants permitted by their construction and geometric forms. Ideally, these motions duplicate the motions of a natural knee. Since these motions are so complex, however, prior art prosthetic knees in all instances exhibited reduced mobility, by virtue of their geometric designs, the provisions of mechanical stops, or both. Thus, sooner or later certain of the opposing and cooperating surfaces of the implants oppose a given motion permitted by the prosthetic knee which allows the transmission of forces other than simple compressive forces between the implants and hence between the implants and the respective bone structures. The transmission of these forces necessarily requires that they be transmitted via the bonding agent or cement between the implants and the femur or the tibia.

Clinical tests and experience have shown that prior art prosthetic knees eventually fail, often not because of a failure of their component parts but because of a failure of the bond between the implants and the bone structures. Applicants believe that the reason for this failure is the marked difference in the modulus of elasticity between the cement and the bone structure to which it bonds the implants. In other words, it appears that in prosthetic knee implants the weakest point is the cement-bone interface (hereinafter sometimes referred to as the "interface").

Upon detailed study and analysis, it appears to applicants that the failure of the cement-bone interface and the resulting loosening of the implants results primarily from the transmission of tensile, shear and tortional stresses. It is difficult to isolate the manner in which tension, shear and torsional stresses are developed; normally however, they are due to a combination of the above-mentioned factors (mechanical stops, limited freedom of motion) together with forces due to friction developed between the implants. On the other hand, studies have shown that compressive stresses which result from the load carried by the knee are better tolerated by the cement and the interface.

Tensional stresses might be the ones least tolerated by the interface and they can develop whenever the restricted mobility of a prosthetic knee or its geometry are such that either one or both of the implants are loaded so as to generate a bending moment at the interface, thereby stressing all or at least part of the interface in tension. Typically, this occurs when the knee joint moves in either the first or the fourth direction discussed above.

Shear stresses at the interface can be developed due to restrictions in the mobility of the knee joint in the above discussed third direction (horizontal sliding) while torsional stresses are developed if there are restrictions in the mobility of the joint in the above discussed second direction, namely rotation.

Eventually it became apparent that the provision of a femoral implant and of a tibial implant alone could not adequately duplicate the motion freedom provided by the natural knee since the function performed by the meniscus in a natural knee is simply deleted. Generally speaking, that function can be defined as giving the joint a certain multidirectional mobility due to the resilient deformability of the meniscus between the relatively rigid femur and tibia.

To overcome this shortcoming, German Offenlegungsschrift No. 2,550,704 proposes a prosthetic knee which includes as a third member disposed between the two implants a meniscal plate. This plate has a lower, flat surface that cooperates with a correspondingly flat surface of the tibia implant and an upper, concave, spherically shaped surface which receives a correspondingly shaped convex surface of the femoral implant. One set of implants is provided for each condyle-plateau pair so that a complete prosthetic knee constructed in accordance with the German publication comprises two sets of implants, each having an independent meniscal plate between them.

The incorporation of the meniscal plate suggested in the German publication, in fact, significantly enhances the mobility of such a prosthetic knee. Especially the provision of cooperating flat surfaces between the tibial implants and the meniscal plate enables relatively free rotational movements between the implants, thereby avoiding the transmission of corresponding forces between them. Instead, torsional forces between the femur and the tibia are transmitted via the appropriate ligaments.

A problem encountered with the construction disclosed in the German publication, however, results from the difficulty of maintaining the flat surfaces of the two tibial implants parallel. If the surfaces are not parallel, relative rotational movements cannot take place, or at least cannot readily take place without transmitting corresponding tortional forces to the implants and thus subjecting the interfaces to tortional stresses which, as above discussed, is to be avoided to prevent a loosening of the implants. Such precise alignment, however, of two independent implants is a most difficult task and it is estimated that only very few orthopedic surgeons are able to assure proper, aligned implantations on a regular basis.

More significantly, the two sets of cooperating spherical surfaces between the femoral implants and the meniscal plates preclude a free-sliding motion between the implants in the above discussed fourth direction, namely abduction or adduction. Instead of permitting relative sliding motion between the implants or between one of the implants and the meniscal discs such motion in fact causes a tilting, thereby transmitting relatively large, eccentrically acting forces to the implants which in effect generate bending moments and thus subject at least portions of the bone-cement interfaces to tension stresses, the type of stresses least tolerated by the interfaces.

Thus, the improved prosthetic knee disclosed in the German publication does not eliminate the persistent problem of preventing a loosening of the implant and the ultimate failure of the knee. At best, it postpones it.

SUMMARY OF THE INVENTION

The present invention is directed to a prosthetic knee which, broadly speaking, substantially eliminates the formation and/or transmission of tension, torsion and/or shear stresses between the implants. In other words, a knee constructed in accordance with the present invention effectively transmits only compressive forces. Consequently, the cement-bone interface between the implants and the supporting bone structures is principally stressed in compression only, the type of stress that is most reliably transmitted by the interface and which causes essentially no loosening thereof even after prolonged use. Thus, implants constructed in accordance with the present invention have a much lesser propensity to fail because the bone-cement interface is not stressed in manners not readily handled by it.

Generally speaking, the present invention accomplishes this by providing both a femoral and a tibial implant and by placing a meniscal plate between opposing surfaces of the implants. The meniscal plate and the implants are constructed so that there is substantially complete relative freedom of motion between them in the above discussed four movement directions. As a result, the components of the prosthetic knee of the present invention are incapable of either generating or transmitting forces that can stress the cement-bone interface in tension, shear or tortion; the cement-bone interfaces are effectively stressed in compression only. Thus, the loosening of the interface, which heretofore constituted the primary source for prosthetic knee failures is effectively eliminated. The prosthetic knee of the present invention, therefore, assures a very long, if not permanent service life.

A principal feature of the prosthetic knee of the present invention is the construction of the meniscal plate and of the tibial platform and, in particular, their cooperating surfaces. The downwardly facing surface (hereinafter sometimes referred to as "undersurface") of the meniscal plate, that is the one which opposes the tibial platform is defined by a convex surface which is compoundly curved so as to permit a substantially unrestrained relative movement between the surfaces when they are in mutual contact. Thus, the under surface is spherically curved, or substantially spherically curved and it is received within a correspondingly shaped, concave surface (hereinafter sometimes referred to as "plateau surface") of the tibial implant.

In use, the meniscal plate is laterally constrained to the femoral implant, as is more fully described below, and is continuously biased towards the tibial implant by the ligaments and muscle structures surrounding and cooperating with the knee joint so that the cooperating convex and concave surfaces of the plate and of the tibial implant are always in mutual engagement.

This engagement of the two surfaces provides a large surface area for the transmission of compressive forces between the implants. This surface area, due to its shape, also provides unrestrained mobility between the mensical plate and the tibial implant so that shear or torsional forces cannot be generated by or transmitted between them. Further, the continuous, spherical character of the surfaces is such that there is effectively no eccentric application of compressive forces between them and, consequently between the implants. Bending moments, acting especially at the cement-bone interfaces, as heretofore encountered with prior art prosthetic knees can, therefore, not develop and tensional forces and stresses caused by such bending moments are prevented. Thus, a prosthetic knee constructed in accordance with the present invention does not and cannot subject the interface to tensional forces.

The lateral stability of the prosthetic knee of the present invention is assured by the concave shape of the plateau surface, which cooperates with the correspondingly shaped convex undersurface of the meniscal plate, and the biasing force applied to them by the surrounding ligaments. Although the cooperating surfaces give the prosthetic knee full lateral mobility (in the above discussed fourth direction, for example) the mobility is limited by the fact that the concave plateau surface forms a recess into which the meniscal plate is forced. In other words, the cooperating surfaces of the tibial implant and the mensical plate form a partial ball-socket type joint and the two members cannot move laterally past each other unless the meniscal plate (and therewith the femoral implant) rises relative to the tibial implant by at least the depth of the recess of concavity of the plateau surface. Except for limited stretching permitted by the ligaments for abduction or adduction motions, such a relative rising of the meniscal plate is prevented by the surrounding ligaments, thereby rendering the prosthetic knee as stable as a natural knee.

It is particularly noteworthy that this limitation on the mobility is not one effected by mechanical stops. Such stops would constitute an unnatural limitation on the mobility of the prosthetic knee. Further, stops would severely stress the cement-bone interfaces in a somewhat unpredictable manner, frequently in tension, shear or torsion, or in a combination thereof with all the adverse consequences for the longevity of the prosthetic knee which flow therefrom. Additionally, the gradual manner in which the mobility of the prosthetic knee is limited more closely simulates the mobility of a natural knee.

The upwardly facing surface of the meniscal plate is defined by two sections which cooperate with two condyle surfaces of the femoral implant. The latter have a surface configuration which is essentially the same as that of the natural condyles. Thus, the condyle surfaces of the femoral implant are convexly shaped in a compound manner while the meniscal plate defines a pair of spaced apart, concave bearing surfaces for them. A section of the meniscal plate between the bearing surfaces engages a generally open space or recess between the condyle surfaces of the femoral implant to constrain the plate to the implant and prevent substantially all relative motions between them except for flexion and extension motions (in the first direction).

Thus, flexion-extension motions of the prosthetic knee of the present invention take place at cooperating surfaces between the femoral implant and the meniscal plate while all other relative motions take place along the cooperating spherically shaped surfaces of the meniscal plate and the tibial implant. The spherical surfaces effectively prevent the transmission of forces other than compressive forces. The former are transmitted in much the same manner as they are transmitted in a natural knee, that is via ligaments and the surrounding muscle structure. As a result, the failure of prosthetic knees due to a failure of the cement-bone interface, as was common with all prior art prosthetic knees, is substantially reduced or eliminated.

Structurally, the femoral and tibial implants are both made of metal, preferably of a chromium-cobalt-molybdenum alloy while the interposed meniscal plate is preferably made of ultra high molecular weight polyethylene. The surfaces of the metal implants which cooperate with surfaces of the meniscal plate are mirror-polished to minimize friction between them.

The femoral implant has downwardly depending extensions which match the natural condyles of the femur and it is of a unitary construction so as to eliminate alignment problems when the surgical implant is made. A space between the condyle portions of the femoral implant is recessed or left open for receiving an intercondylar eminence or protuberance of the mensical plate.

The downwardly facing undersurface of the meniscal plate is, as above described, convex and fits exactly within the concave plateau surface of the tibial implant.

Preferably, the meniscal plate can be manufactured in a variety of thicknesses, say in increments of 5 mm from 5 to 25 mm so that a proper one can be selected when the implant is made to assure the tightness of the joint while enabling the surgeon to compensate for variations in joint dimensions, variations in the amount of bone that had to be removed for the implant, the patient's ligament and muscle characteristics, etc.

Preferably, the surfaces of each metallic implant which come in contact with and which are cemented to bone structure have recesses, grooves, etc. to both facilitate the retention of cement during their implanting and to provide spaces into which bone may grow to mechanically interlock it with the implant and to provide a connection which is as secure as possible.

BRIEF DESCRIPTION OF THE DRAWINGS

FIG. 3 is a side elevational view, in section, of the prosthetic knee shown in FIG. 2 and is taken on line 3—3 of FIG. 2;

FIG. 4 is an exploded, perspective-front elevational view of the components of the prosthetic knee shown in FIGS. 2 and 3.

DESCRIPTION OF THE PREFERRED EMBODIMENTS

Figure 1A:
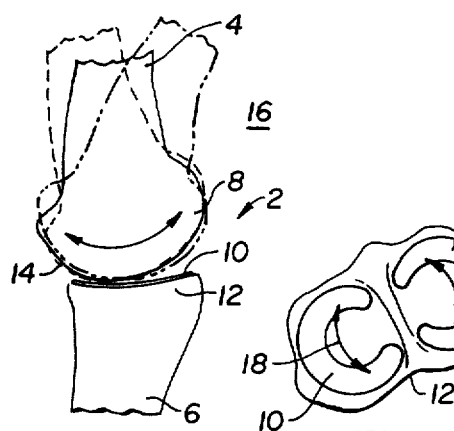
FIGS. 1A–D are schematic illustrations of motions permitted by a natural human knee.

Referring to FIGS. 1A-D, a natural human knee 2 is generally illustrated. For simplicity, only the femur 4 and the tibia 6 are shown the fibula, which extends generally parallel to the tibia is of no importance for an understanding of the working of a knee and is, therefore, not shown. At the lower end the femur terminates in a pair of side-by-side femoral condyles 8 which are received by dished in meniscii carried on an upper end of the tibia which defines a tibial plateau 12. A natural human knee also includes a patella which is not illustrated in FIGS. 1A-D.

The perhaps most common and widely recognized motion of the knee is in flexion or extension and that motion is generally illustrated in FIG. 1A. The motion is a rocking type motion in the course of which downwardly facing, convex and compoundly curved surfaces 14 of the condyle slide and roll over an appropriately shaped, concave surface defined by each meniscus 10 and the tibial plateau 12. Flexion and extension of the knee joint takes places in the plane 16 in which FIG. 1A is drawn, also shown in FIG 1D, which is generally vertical (when the patient stands in an upright position) and which is further generally parallel to the longitudinal extent of the condyle surfaces. Flexion and extension is thus a generally pivotal movement between the femur and the tibia although the movement does not take place about a single pivot axis but rather along a curved path defined by the condyle surfaces and the shape of the cooperating surfaces of the meniscii and the tibial plateau. For ease of reference this motion permitted by the natural knee is sometimes referred to as a motion in the "first direction".

Figure 1B:
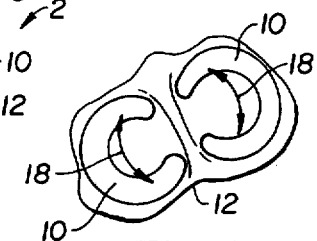

FIG 1B is a general plan view of the tibial plateau only, schematically illustrates the location and shape of natural meniscii 10, and the arrows 18 illustrate relative rotational motion permitted by knee joint 2 about a generally vertical axis (when the patient is in the upright position) over a limited arc defined by the cooperating surfaces of the condyles, meniscii and tibial plateau. For ease of reference this rotational motion permitted by the natural knee is sometimes referred to as a motion in the "second direction"

Figure 1C:
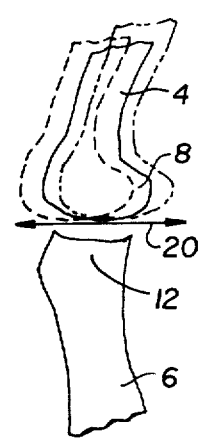

FIG. 1C illustrates another motion permitted by the natural knee, a very limited, relative sliding motion (which, in a knee is accompanied by a rolling motion) between the condyles and the tibial plateau in a plane substantially perpendicular to the fully extended tibia and femer, e.g. in a generally horizonal plane when the patient is standing. This relative sliding motion is illustrated in FIG. 1C by arrow 20 and is sometimes referred to as a motion in the "third direction".

Figure 1D:
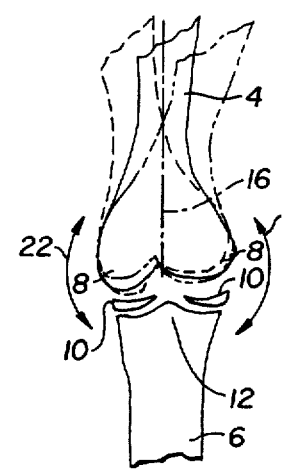

FIG. 1D shows yet another motion permitted by the natural knee, namely a lateral sliding or rocking type motion illustrated by arrows 22. This motion, frequently referred to as abduction and adduction, is sometimes referred to as a motion in the "fourth direction".

Referring now to all figures, a prosthetic knee 24 constructed in accordance with the present invention affords the patient in whose leg such a prosthetic knee has been implanted a degree of mobility which is substantially the same as that provided by the natural knee. This, however, is not accomplished by attempting to structurally duplicate a natural knee. Instead, prosthetic knee 24 merely duplicates the functions of the natural knee; structurally the prosthetic knee differs from a natural knee in several important respects to take into account and alleviate the problems one is faced with when a prosthetic knee is implanted. In particular, the prosthetic knee of the present invention is shaped so that it substantially eliminates stresses other than compressive stresses at the cement-bone interface.

Prosthetic knee 24 generally comprises a femoral implant 26 which is secured to the patient's femur 4 as further described below; a tibial implant 28 secured to the upper end of the patient's tibia 6; and an intermediate meniscal plate 30. As is more fully described below it will be observed that the interface between the tibial implant and the meniscal plate is defined by cooperating spherically shaped, concave and convex surfaces, respectively, when enable sliding motions along these surfaces between the tibial implant and the meniscal plate and, thereby, between both implants. This free sliding motion is not present on a natural knee; however, a natural knee is not confronted with the earlier discussed loosening problems between the implants and the bone structure at the cement-bone interface. Thus, in a natural knee, for example, abduction and adduction in the fourth direction can take place in the form of a rocking motion in which one or the other condyle surface 14 effectively "lifts off" its associated meniscus and tibial plateau surface. The supporting bone structures have sufficient strength to support such eccentric loading.

However, if such loading is applied to an implant, say the tibial implant 28, the eccentric loading has the effect of subjecting the cement-bone interface immediately beneath the eccentrically loaded condyle to an increased compressive stress. As the eccentric loading increases the compressive stress at the cement-bone interface underlying the other condyle (the one which is effectively "lifted off") first decreases and then converts into tension stress. It is these tensional stresses which, over extended time periods, lead to a loosening of the cement-bone interface. However, such an eccentric loading is not possible in the prosthetic knee 24 of the present invention since a motion in the fourth direction does not result in a rocking motion but rather in a relative sliding motion between the spherically shaped cooperating surfaces of the tibial implant and the meniscal plate. As a result, even under adduction or abduction the cement-bone interfaces between the implants and the surrounding bone structures continue to be stressed in compression, a stress mode which does not adversely affect the interface and which can be tolerated for indefinite periods.

Figure 2:
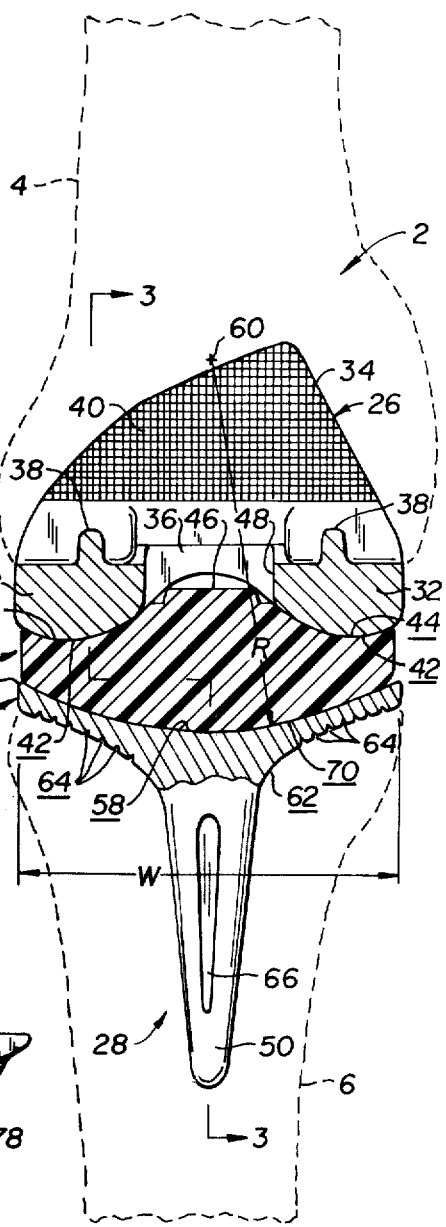
FIG. 2 is a rear elevational view, in section, of a prosthetic knee constructed in accordance with the present invention.

Referring now specifically to FIGS. 2-4, the femoral implant has a somewhat U-shaped configuration, as is best seen in FIGS. 3 and 4, and is defined by a pair of spaced apart condyle sections 32 which are interconnected by and integrally constructed with a front plate 34 and which define between them a slot or recess 36. The side of the femoral implant facing the femur includes pins 38 for insertion into appropriately formed openings in the femur. Further, the femur facing sides include grooves, depressions and the like, generally identified by reference numeral 40, for the retention of cement to facilitate the connection of the implant to the femur in the manner more fully described below.

The downwardly facing side of the femoral implant and, in particular of the condyle sections 32 define convex, compoundly curved condyle surfaces 42 which conform as closely as possible to the shape of the natural condyle surfaces. Thus, condyle surfaces 42 are complex surfaces with continuously changing radii of curvature so that sliding motions along the longitudinal extent of the condyle surfaces (shown in FIG. 3) duplicate the flexion-extension of a natural knee.

The femoral implant is preferably made of a biologically inert chromium-cobalt-molybdenum alloy and the condyle surfaces 42 are mirror polished to assure a low friction sliding interengagement with meniscal plate 30.

The meniscal plate is of a one-piece construction, preferably made from ultra-high molecular weight polyethylene. Its upwardly oriented face 45 includes a pair of spaced apart, concave, compoundly curved depressions 44 that form bearing surfaces for the condyle surfaces 42 of the femoral implant. Disposed between the bearing surfaces is an upwardly extending protuberance 46 that is positioned and dimensioned so as to engage sides 48 of the condyle sections 32 which face recess 36. When the femoral implant 26 and the meniscus plate 30 are biased against each other so that condyle surfaces 42 rest in the spherical depressions 44, the protuberance 46 pevents substantially all relative movements between the femoral implant and the meniscal plate other than relative sliding motions between the two parts along the condyle surfaces, that is in the flexion-extension plane of the prosthetic and natural knee (No. 16 in FIG. 1D).

The femoral implant and the meniscal plate are shaped so that sliding motion, which is essentially a pivotal motion as above described, can take place over the full pivotal range of the natural knee, e.g. through an arc of approximately 135°. Yet, substantially no relative motions in a lateral direction between the femoral implant and the meniscal plate are possible by virtue of the extension of protuberance 46 into recess 36.

The tibial implant 28 has a generally T-shaped configuration and is defined by a downwardly extending, tapered spike 50 and a plate member 52 which functionally replaces the natural tibial plateau of tibia 6. The spike is inclined relative to the plate member by an angle "α" of about 5° to 15°, and preferably of about 10°.

Figure 5:
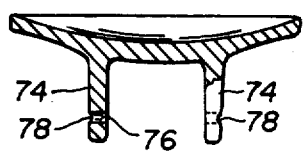
FIGS. 5 and 6 are front and side elevational views which illustrate an alternative construction of the tibial component of the prosthetic knee.
Figure 6:
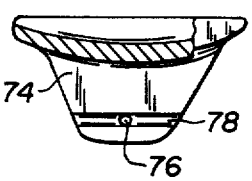

Alternatively the spike of the tibial implant may be replaced by a pair of spaced apart, downwardly depending generally parallel flanges 74 as is shown in FIGS. 5 and 6. The flanges are provided with holes 76 and with grooves 78 for retaining filler material to cement the implant to the bone structure.

The plate member has a generally planar boundary 54 and a generally rectangular plan configuration except for an arcuate cutout 56 along its aft boundary. The upwardly facing side of the plate member is defined by a concave, spherically shaped plateau surface 58 which has a radius of curvature "R". The origin 60 of the radius lies on the same side of the plate member as the femoral implant, i.e. it is "above" the plate member. Further, it lies on a center line which coincides with the lateral and longitudinal centers of the plate member as defined by its width "W" and depth "D" and which further is on or proximate the longitudinal axis of the prosthetic knee 24 when its components are fully extended (as illustrated in FIGS. 2 and 3). Further, the center line also coincides with the center line of spike 50 in the rear elevation as seen in FIG. 2.

As is the case with the femoral implant, the tibial implant 28 is of a uniform, i.e., one-piece construction, made of biologically inert, high strength metal such as the above-referenced chromium-cobalt-molybdenum alloy and the concave plateau surface 58 has a mirror polish to minimize friction during relative slidable movements of meniscal plate 30.

The underside 62 of the tibial implant has grooves or undercuts 64 to facilitate the bonding of the implant to surrounding bone structure. For a like purpose, spike 50 may be provided with longitudinally extending, cement receiving grooves 66.

The meniscal plate 30 has a plan configuration shaped complementary to that of plate member 52, that is it has a generally rectangular outline but it is of a slightly smaller size to allow it to move relative to the plate member without protruding past the boundary 54 thereof. The meniscal plate includes at its aft side an arcuate cutout 68 which roughly corresponds in size to the arcuate cutout 56 in the tibial implant. The meniscal plate has an undersurface 70 which is convex and spherically shaped and mates with the concave plateau surface of the tibial implant. The undersurface has the same radius of curvature "R". Although the undersurface is preferably a continuous surface, if desired, it can also be defined by two or more surface sections, separated by grooves, for example, so long as the surface section forms apart of a common spherical surface of a radius of curvature "R".

The plate further has an effective height "H" (measured from the bottom of concave bearing surface 44 to the apex of undersurface 70 as is illustrated in FIG. 3) selected to maintain the desired spacing between the femoral and the tibial implants as is further discussed below.

The prosthetic knee 2 is implanted as follows. First, the patient's knee is surgically opened and portions of the lower end of his femur and of the upper end of his tibia are removed. The extent of bone removal will vary from patient to patient. At least, however, sufficient bone is removed so that a meniscal plate 30 of minimal thickness, say of a thickness "H" of 5 mm may be placed between the femoral and the tibial implants 26, 28. Holes are further formed in the respective bones to receive pins 38 of the femoral implant and spike 50 (or fins) of the tibial implant. Thereafter, a suitable filling material such as methylmethacrylate cement is applied to the surfaces of the bones and the implants which will come into contact and the implants are inserted. Upon the hardening of the cement the implants are rigidly secured to the bones and in essence become structurally integrated therewith.

A meniscal plate 30 is now placed between the implants so that the undersurface 30 of the plate is received within the recess defined by the concave plateau surface 58 and the condyle surfaces 42 of the femoral implant bear against the concave bearing surfaces 44 of the meniscal plate. This requires that the effective height "H" of the meniscal plate be appropriately chosen to maintain a sufficient spacing between the implants so that the patient's ligaments spanning across the knee joint are tensioned. The tensioned ligaments in turn bias the cooperating, relatively movable surfaces of the implants and the meniscal plate into mutual contact to form a secure and stable prosthetic knee.

To facilitate the selection of the proper meniscal plate height, it is preferred that the surgeon performing the implant be furnished with a set of meniscal plates which have varying heights "H" but which are otherwise identical. For example, a set of meniscal plates may be provided which have heights of 5, 10, 15, 20, 25, etc. mm. Other gradations in the heights may, of course, be chosen.

once the surrounding tissue has healed, the prosthetic knee provides the patient with substantially the same mobility as a natural knee. Flexion and extension of the knee takes place through corresponding slidable movement between condyle surfaces 42 and meniscal plate bearing surfaces 44. Flexion and extension is thus performed by surfaces which are a substantial duplicate of corresponding surfaces found in the natural knee. Accordingly, the condyle surfaces, particulaly in regard to their longitudinal extent, that is in a direction parallel to plane 16 (see FIG. 1D) are formed so as to be identical to or correspond as closely as possible to the condyle surfaces of the natural knee.

During flexion and extension, the natural knee also goes through a certain amount of rotational motion. A corresponding motion takes place in the prosthetic knee of the present invention between the plateau surface 58 and the undersurface 70 of the meniscal plate. Similarly, relative sliding motion (in the third direction) or lateral abduction and adduction (in the fourth direction) are permitted by the prosthetic knee by virtue of corresponding sliding motions between the plateau surface and the undersurface of the meniscal plate.

It should be noted that at all times, substantially the full surface areas of the plateau surface 58 and of the undersurface 70 are in contact, thereby providing large contact areas and correspondingly small contact pressures. Further, compressive forces are substantially evenly distributed between the femur and the tibia over the full surface areas, forces are substantially evenly applied to both condyle surfaces 42 at all times, and the formation of forces which eccentrically act in the above summarized manner on either implant are avoided.

The stability of the prosthetic knee is assured by virtue of the recess or concavity of the plateau surfaces 58 into which the tensioned ligaments bias the convex undersurface 70 of the meniscal plate. To illustrate the point and disregarding movements beyond the fully extended position, which are prevented by the patella in the normal manner, slidable motion (in the third direction) between the tibial implant and the meniscal plate can only take place if the distance between the femur and the tibia were permited to increase. As in the natural knee, the ligaments oppose such an increase beyond very narrow limits. The ligaments similarly restrict movements in the fourth direction (abduction and adduction) to narrow limits of a few degrees since any such movement would necessitate a significant lengthening of the ligaments. Thus, as in the natural knee, the ligaments limit such movements.

Further, a lateral displacement of the meniscal plate relative to either implant in all directions other than the first direction is prevented by the interengagement between the protuberance 46 of the plate and the cooperating recess 36 of the femoral implant.

A lateral displacement of the meniscal plate relative to either implant in the first direction is prevented by the depressions or concavity formed by bearing surfaces 44 and plateau surface 58 into which the condyle surfaces 42 and the convex undersurface 70, respectively, extend since the tensioned ligaments continuosly bias the latter into the depressions and concavity. Thus, in order for a lateral displacement of the meniscal plate to take place the implants would have to be forced apart which is prevented by the tensioned ligaments.

In effect, therefore, the ligaments maintain the components of the prosthetic knee in engagement and so long as such engagement is present the cooperating convex and concave surfaces form socket-type joints which assure the stability of the knee at all times. Yet, as above described, they provide the required freedom of motion for the knee without relying on undesirable stops or the like for stability.

Dimensionally, the tibial implant is sized to roughly correspond to the dimension of the tibial plateau of a natural knee. In a standard tibial implant, the plate member 52 of the tibial implant has a width "W" of 2.50", a depth "D" of 2.00", amd a radius of curvature "R" for plateau surface 58 of 2.50" or more. This results in a maximum depth "T" for concavity formed by the plateau surface of about 3/16". A depth "T" in the range of about $\frac{1}{8}$" to about 5/16" appears to be most desirable.

The meniscal plate 30 is similarly dimensioned although it is given a lesser width and depth so as to allow it to slide relative to the tibial implant along plateau surface 58. For a tibial plate member dimensioned as above set forth, the meniscal plate should have a width (parallel to "W") of no more than about 2.4" and a depth (parallel to "D") of no more than about 1.56". As for bearing surfaces 44 of the meniscal plate which receive condyle surfaces 42 of the femoral implant good results have been obtained by extending the depressions over substantially the full depth (in a direction parallel to "D") and compoundly curving the recesses with a transverse radius (in the direction of "W") of approximately 0.71", a longitudinal radius (parallel to "D") of 1.25" which results in a depth for the recess (measured from upwardly facing surface 45) of about $\frac{1}{8}$ to 3/16".

We claim:

1. A prosthetic knee for implantation in a body comprising a femoral implant for connection to a femur defining a pair of spaced apart, convexly curved condyle sections; a meniscal plate having a pair of spaced apart, concavely curved bearing surfaces for cooperation with the condyle surfaces and permitting the latter to move relative to the former in a knee flexionextension plane; and a tibial implant for connection to the patient's tibia, the tibial implant including a plateau facing towards the femoral implant and having a concave, compoundly curved plateau surface; the meniscal plate further including a convex undersurface shaped complementarily to the plateau surface, the plateau surface and the undersurface having a shape permitting a substantially unrestrained relative sliding motion between the plateau surface and the undersurface when the plateau surface and the undersurface are biased against each other.

2. A prosthetic knee according to claim 1 including means defined by the femoral implant and by the meniscal plate for limiting relative motions between them to relative motions in substantially the flexion-extension plane.

3. A prosthetic knee according to claim 1 wherein the undersurface of the meniscal plate is a continuous surface.

4. A prosthetic knee according to claim 1 wherein the undersurface of the meniscal plate is defined by a plurality of distinct surfaces, the surfaces having a common center of curvature.

5. A prosthetic knee according to claim 1 wherein the concave plateau surface and the undersurface of the meniscal plate have a common center of curvature.

6. A prosthetic knee according to claim 5 wherein the plateau surface has a depth relative to its boundaries of at least about $\frac{1}{8}$".

7. A prosthetic knee according to claim 1 wherein surfaces of the femoral implant and of the tibial implant in contact with bone structures each include a plurality of undercuts.

8. A prosthetic knee according to claim 1 wherein the plateau surface has a substantially spherical shape.

9. A prosthetic knee comprising in combination: a femoral implant having a pair of spaced apart condyle sections defining spaced apart, convex, compoundingly curved, substantially parallel condyle surfaces and means, integrally constructed with the condyle sections, for rigidly interconnecting the sections, the femoral implant further including means for placing the implant in contact with femoral bone structure and for immovably securing the implant to such bone structure, the implant defining a recess between the condyle surfaces; a tibial implant having platform means defining a concave, substantially spherically shaped plateau surface and including means for immovably securing the tibial implant to tibial bone structure; the implants being constructed of a metal, the condyle surfaces and the platform surface having a polished mirror finish; and a meniscal plate constructed of a plastic material, the plate defining a pair of spaced apart, concave condyle bearing surfaces positioned and shaped to engage the condyle surfaces of the femoral implant and to permit relative sliding motion between the condyle surfaces and the concave bearing surfaces in a direction generally parallel to the condyle surfaces, the meniscal plate further including means disposed between the concave surfaces and shaped to protrude into the recess defined by the femoral implant to limit relative movements between them to movements which are generally parallel to the condyle surfaces, the meniscal plate further defining an undersurface which faces the plateau surface and which has a convex, substantially spherical shape, the plateau surface and the undersurface having like radii of curvatures so as to permit substantially unrestrained sliding motion between them while retaining substantially their fully respective surfaces in mutual engagement to thereby substantially limit the transmission of forces between the undersurface and the plateau surface and, thereby, between the implants to compressive forces and provide relatively large surface areas for the transmission of the compressive forces between the undersurface and the plateau surface; whereby when surgically implanted, the implants and the meniscal plate are biased into mutual engagement by the patient's ligaments and muscle structurs, flexion and extension movements of the patient's knee take place through relative movement between the condyle surfaces and the concave bearing surfaces of the meniscal plate while all other relative movements between the implants take place through corresponding sliding movements between the plateau surface of the tibial implant and the undersurface of the meniscal plate; and whereby further the biased engagement of the implants and the meniscal plate limits the extent of relative sliding motion between the plateau surface and the undersurface.

10. A prosthetic knee comprising a femoral implant for connection to the femur of a patient defining a pair of spaced apart, convex, compoundly curved condyle surfaces and a recess therebetween; a tibial implant for connection to the tibia of the patient defining a plate member oriented generally perpendicular to the tibia and including a boundary and a concave, substantially spherically shaped and continuous surface recessed into the member, the boundary having an extent which approximates the extent of the patient's natural tibial plateau in a transverse direction relative to the length of the tibia; each implant being of a unitary construction; and a single, integrally constructed meniscal plate disposed between the implants and having a pair of concave bearing surfaces positioned and shaped to engage the condyle surfaces of the femoral implant, a protrusion extending into the recess for limiting relative motion between the femoral implant and the meniscal plate to motions corresponding to flexion and extension movements of the patient's natural knee, the meniscal plate further including a convex undersurface for engaging the recessed surface, all portions of the undersurface engaging the recessed surface having a substantially spherical shape and the same radius of curvature as the recessed surface of the tibial implant so that the undersurface can protrude into the recessed surface and, while in engagement therewith, can slide relative thereto; whereby, upon implantation of the prosthetic knee, the patient's knee ligaments and associated muscles bias the undersurface into engagement with the recessed surface and thereby retain the undersurface within a recess in the tibial implant defined by the recessed surface and maintain load transmitting contact over a relatively large area of the recessed surface and the undersurface while effectively limiting the transmission of forces between them to the transmission of compressive forces.

11. A prosthetic knee according to claim 10 wherein the plate member has a generally rectangular outline.

12. A prosthetic knee according to claim 11 wherein the plate member has a width of approximately 2½" and a depth in the direction of flexion and extension movements of approximately 2".

13. A prosthetic knee according to claim 12 wherein the radius of curvature of the recessed surface and of the undersurface is at least about 2½".

14. A prosthetic knee according to claim 12 wherein the meniscal plate has a generally rectangular outline complementary in shape to the outline of the plate member, the meniscal plate having a width and a depth in the direction of the width and the depth of the plate member of no more than about 2.4" and 1.56", respectively.

15. A prosthetic knee according to claim 11 wherein the meniscal plate has a generally rectangular outline complementary in shape to but smaller than the outline of the plate member.

16. A prosthetic knee according to claim 10 wherein the recessed surface defines a concavity, the concavity having a depth relative to the boundary in the range of between about ⅛" to about 5/16".

17. A prosthetic knee according to claim 10 wherein the bearing surfaces define depressions having a depth of between about ⅛" to 3/16".

18. A prosthetic knee for replacement of a natural human knee through implantation, the prosthetic knee comprising in combination a femoral implant defining a pair of spaced apart, convex condyle surfaces shaped to substantially correspond to condyle surfaces of a natural human knee; a mensical plate having an upper side facing the femoral implant, the upper side including a pair of spaced apart, concave depressions for engaging and cooperating with the condyle surfaces of the femoral implant to permit relative flexion and extension motions only between the femoral implant and the meniscal plate; and a tibial implant disposed on a side of the meniscal plate opposite the femoral implant, the tibial implant including a plate member oriented transversely to an axis through the fully extended prosthetic knee, the plate member having a generally rectangular outline defined by a depth in the direction of the flexion and extension motions of up to about 2" and a width in a direction perpendicular thereto of up to about 2½", the plate member and the meniscal plate defining between them an interface along which the plate member and the meniscal plate can move with respect to each other in a multitude of substantially circular paths, all paths having a common origin located proximate to the axis of the fully extended prosthetic knee so that relative motions between the tibial implant and the meniscal plate and, therewith, the femoral implant can take place at the interface for all knee motions other than flexion and extension motions; and whereby upon the implantation of the prosthetic knee in a patient, the patient's natural ligaments and muscle structure firmly bias the implants and the meniscal plate into engagement and the cooperating convex and concave surfaces of the interface and of the condyle surfaces and bearing surfaces impart stability to the prosthetic knee.

19. A prosthetic knee accordng to claim 18 wherein the origin is spaced from the interface at least about 2½".

20. A prosthetic knee according to claim 18 wherein the origin is disposed on the same side of the plate member as the femoral implant.

* * * * *